US00PP26368P3

(12) United States Plant Patent
Banados Ortiz et al.

(10) Patent No.: US PP26,368 P3
(45) Date of Patent: Feb. 2, 2016

(54) BLACKBERRY PLANT NAMED 'CAMILA'

(50) Latin Name: *Rubus subgenus Rubus*
Varietal Denomination: Camila

(71) Applicant: Hortifrut S.A., Estero, FL (US)

(72) Inventors: Maria Pilar Banados Ortiz, San Fernando (CL); Alejandra Andrea Salgado Rojas, Santiago (CL); John Reuben Clark, Fayetteville, AR (US)

(73) Assignee: Hortifrut S.A., Santiago (CL)

( * ) Notice: Subject to any disclaimer, the term of this patent is extended or adjusted under 35 U.S.C. 154(b) by 163 days.

(21) Appl. No.: 13/694,787

(22) Filed: Jan. 4, 2013

(65) Prior Publication Data

US 2014/0196182 P1 Jul. 10, 2014

(51) Int. Cl.
*A01H 5/08* (2006.01)

(52) U.S. Cl.
USPC ..... Plt./203
CPC ..... *A01H 5/0887* (2013.01)

(58) Field of Classification Search
USPC ..... Plt./203
CPC ..... A01H 5/0887; A01H 5/08
See application file for complete search history.

(56) References Cited

U.S. PATENT DOCUMENTS

| | | | |
|---|---|---|---|
| PP6,679 | P | 3/1989 | Moore |
| PP11,865 | P2 | 5/2001 | Clark et al. |
| PP15,788 | P2 | 6/2005 | Clark et al. |
| PP16,989 | P3 | 8/2006 | Clark et al. |
| PP22,449 | P3 | 1/2012 | Clark |
| 2012/0151645 | P1 | 6/2012 | Clark et al. |

OTHER PUBLICATIONS

Hargreaves, Rebuen, "Hargreaves Plants: Reuben Blackberry," pp. 1-3, Oct. 25, 2012, http://reubenblackberry.com/.

Clark, John R. et al., "'APF-45' Primocane-fruiting Blackberry," HortScience 46(4): 670-673, 2011.

Clark, John, "Primocane-fruiting Blackberry Breeding," HortScience vol. 43(6), pp. 1637-1639, Oct. 2008.

*Primary Examiner* — Kent L Bell
(74) *Attorney, Agent, or Firm* — King IP Law; Joshua King

(57) ABSTRACT

A new and distinct primocane-fruiting cultivar of Blackberry plant named 'Camila' as described and illustrated herein. Distinctive characteristics of 'Camila' include its earliness, thornless stems, large sized fruit and sweetness without bitter aftertaste.

3 Drawing Sheets

BACKGROUND AND SUMMARY

Blackberries are a well-known, aggregate fruit enjoyed by many throughout the world. One example of an existing blackberry variety is 'APF-8', which is marketed as "Prime Jan®", U.S. Plant Pat. No. 15,788. Other examples of existing, patented blackberry varieties are 'Navaho', U.S. Plant Pat. No. 6,679 and 'APF-12', U.S. Plant Pat. No. 16,989 which is marketed as "Prime Jim®".

Compared to 'APF-8' based on some typical results, the present cultivar, 'Camila' (also known as "HFM-5"), and 'APF-8' are both primocane-fruiting blackberries, but 'Camila' bears fruit on primocanes about one (1) week earlier than 'APF-8'. In addition, plants of 'Camila' have a slightly lower density of spines on the stems and the growth rate is somewhat less than that of 'APF-8'. The fruits of 'Camila' are much sweeter, with higher firmness, have almost no bitter aftertaste and have less acidity than 'APF-8'. The average degrees Brix (° Bx) and percent acidity of the juice of primocane fruits of 'Camila' is 15.1° Bx and 0.7%, respectively, versus 9.8° Bx and 1.3% for primocane fruits of 'APF-8'. The postharvest quality of primocane fruits of 'Camila' is also higher than that of the primocane fruits of 'APF-8': After seven (7) days storage at 5° C., the primocane fruits of 'Camila' are firmer than those of 'APF-8' with only 27% of berries of the former showing leaking juice, versus 60% leaking fruits in the case of 'APF-8'.

Compared to 'Navaho' based on some typical results, the present cultivar, 'Camila', bears fruits on both floricanes and primocanes, whereas 'Navaho' bears fruits only on floricanes. Accordingly, the following comparisons to 'Navaho' involve floricane fruit of 'Camila'. The vegetative growth of 'Camila' is considerably more vigorous than that of 'Navaho'. The canes of 'Camila' are erect, thick and thorny, whereas those of 'Navaho' are semi-erect, thin, and thornless. Floricane fruits of 'Camila' are 5.9 g and 2.8 cm long versus 3.0 g and 1.5 cm for 'Navaho'. The fruit of 'Camila' matured four (4) weeks earlier than those of 'Navaho'; the date of first ripening of 'Camila' in Central Chile is week 49 (e.g. the second week of December) versus week 1 (e.g. the first week of January) for 'Navaho'.

The present cultivar, 'Camila', provides one or more advantages compared to these and/or other blackberry varieties such as one or more of an early maturity and better blackberry fruit for at least some purposes.

BRIEF DESCRIPTION OF THE PHOTOGRAPHS

DETAILED DESCRIPTION

Figure 1:
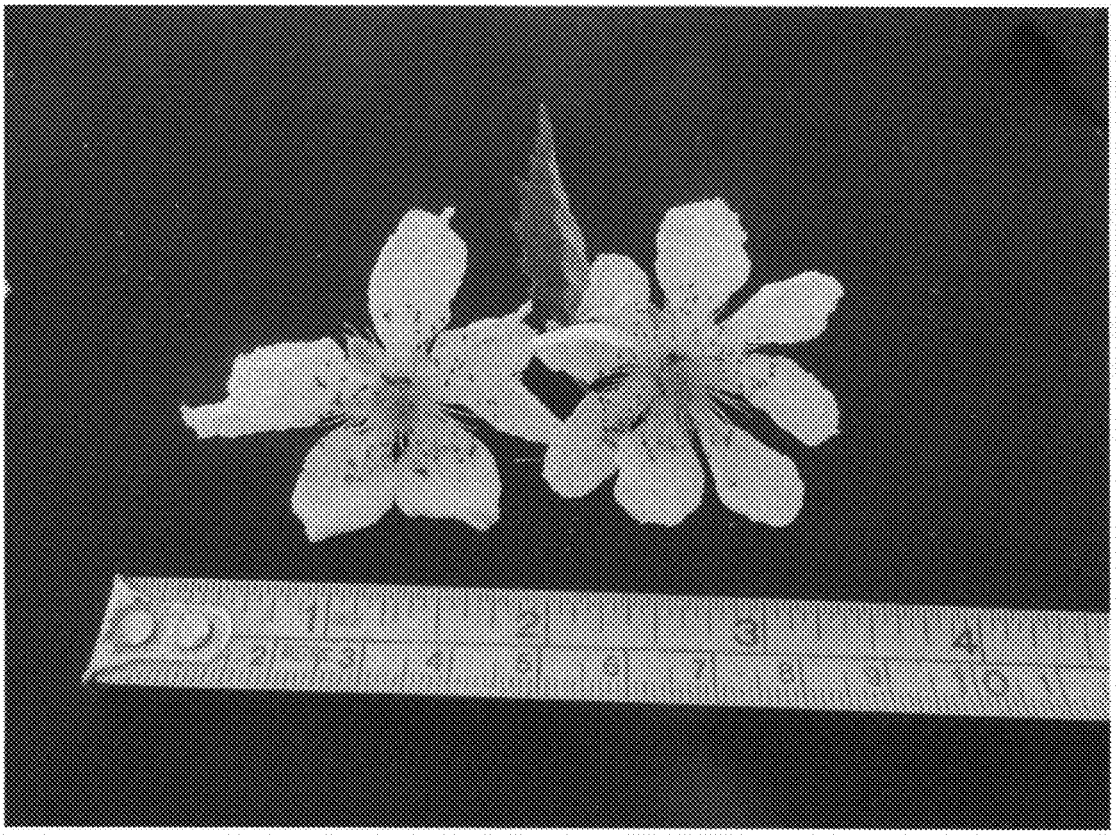
FIG. 1 is a photograph showing primocane flowers of the Blackberry cultivar 'Camila'. This photograph was taken on 22 Mar. 2012 (in Chile).
Figure 2:
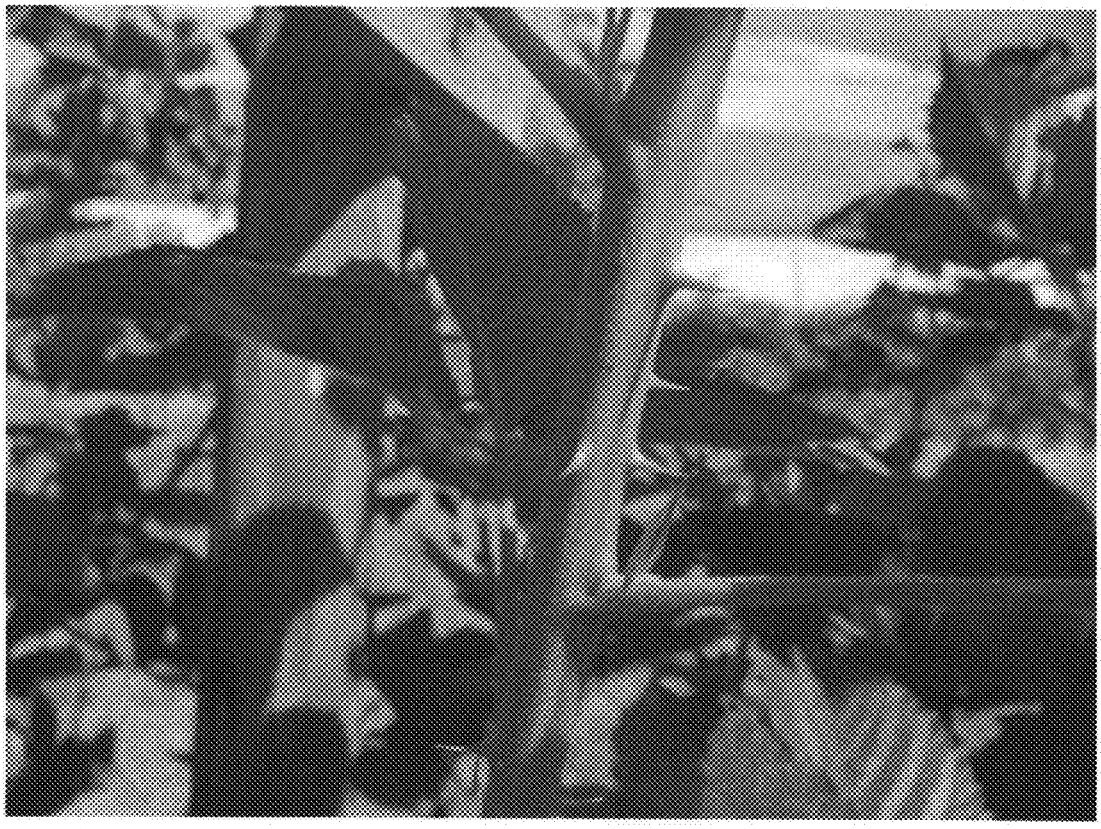
FIG. 2 is a close-up photograph of a primocane shoot of the Blackberry cultivar 'Camila' showing primocane color and spine density. This photograph was taken 21 Mar. 2012 (in Chile).
Figure 3:
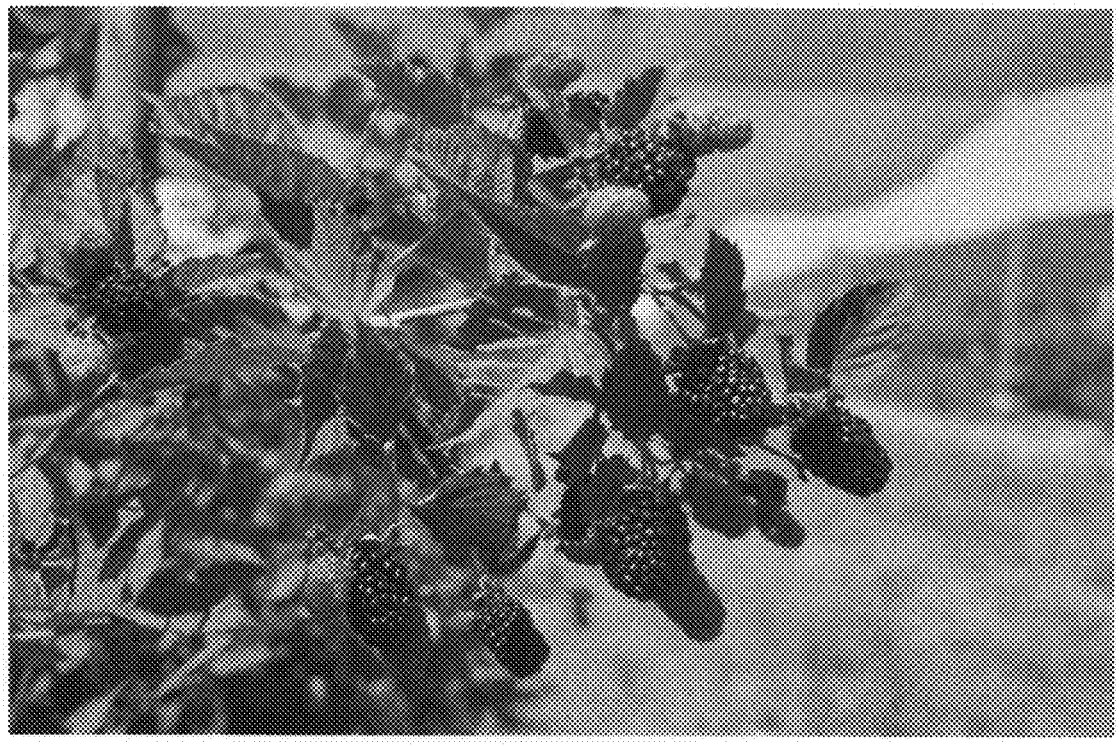
FIG. 3 is a close-up photograph of primocane fruits. This photograph was taken 16 Feb. 2012 (in Chile).

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are generally from specimen plants that were planted in August 2008 and later at Nogales, Fifth Region, Chile. References to color refer to The R.H.S.—Fifth Edition.

Cultivar name: 'Camila'.

Classification:

*Family*.—Rosaceae.

*Botanical name*.—*Rubus* subgenus *Rubus*.

*Common name*.—Blackberry.

Parentage: Note: The parents and 'Camila' have not been evaluated side-by-side. The data about 'Camila' is from Chile and the data for the parents are from Arkansas, USA.

*Female parent*.—Name: Name: 'APF-77' (proprietary, and marketed under the trademark Black Magic™). U.S. Plant patent application Ser. No. 13/374,444 filed 29 Dec. 2011. Comparing 'APF-77' grown in Arkansas to 'Camila' grown in Chile, the average floricane berry weight of 'APF-77' is 6 to 7 grams compared to 5.9 grams for 'Camila'. Floricane first bloom date and first ripe date for 'APF-77' appear to be about a week to 10 days earlier compared to 'Camila': the floricane first bloom date for 'APF-77' is 1 April (Northern Hemisphere) versus 10 October (Southern Hemisphere) for 'Camila' while the first ripe date for 'APF-77' is 2 June versus 8 December for 'Camila'. The first primocane bloom date for 'APF-77' is 10 June (Northern Hemisphere) compared to 20 December for 'Camila' (Southern Hemisphere), and the first primocane ripe fruit are 15 July (Northern Hemisphere) for 'APF-77' compared to 10 February (Southern Hemisphere) for 'Camila'. Soluble solids in primocane fruit of 'Camila' is 15.1° Brix compared to 10.2° Brix for 'APF-77'.

*Male parent*.—Name: 'APF-109T'. US plant patent: unpatented. Comparing 'APF-109T' grown in Arkansas to 'Camila' grown in Chile, 'APF-109T' is thornless and has a smaller berry than 'Camila': floricane berries for 'APF-109T' average 4.4 grams versus 5.9 grams for 'Camila' berries. The harvest window for such floricane fruit appears to be similar or perhaps that of 'Camila' would be slightly earlier: the window is about 16 June (Northern Hemisphere) for 'APF-109T' compared to about 8 December for 'Camila' (Southern Hemisphere). The soluble solids of floricane fruit of 'Camila' are higher: 11.3° Brix for 'Camila' compared to those of 'APF-109T' which are 9.2° Brix.

The cross for 'Camila' was made in 2006 near Clarksville, Ark., USA. It was a controlled hand pollination of the female parent ('APF 77')×APF 109T (male parent). Resultant seedlings were germinated in a nursery near Hijuelas, Fifth Region of Valparaiso, Chile during the southern hemisphere summer of 2006-07. 285 individual seedlings from this cross were planted in the field near Nogales, Fifth Region of Valpariso, Chile between December 2007 and January 2008. The first evaluation of these seedlings was in early summer (November) 2008 and continued through April 2009. The selection that became 'Camila' was selected in 2009 because the seedling stood out for its very good flavor and the early maturity on primocanes.

Camila was first asexually propagated by planting root pieces horizontally in containers containing a bark/peat mix in August 2009 in a greenhouse in Macul, Santiago, Chile. Etiolated shoots that emerged from the root pieces were put in a peat/perlite mix and rooted under humid conditions (covered by clear polyethylene plastic). 'Camila' has also been asexually reproduced using in vitro culture. Propagated plants have retained the original characteristics.

Field observations were made in 2009 and later, mostly in Nogales, Chile, including evaluation over three primocane fruiting cycles and two floricane fruiting cycles between January 2009 and April 2011. 'Camila' consistently showed above average horticultural traits and was consistently at the top for taste tests for flavor. For firmness readings, firmness was ranked by on a scale of one to five, with 1 being very firm, and 5 being very soft.

General description: The 'Camila' blackberry is characterized for its early fruit maturity, both on floricanes and on primocanes. The floricane crop begins to ripen during the first week of December (Central Chile). The primocane crop begins to ripen during the second week of February (Central Chile). The fruit has very good (sweet) flavor. The fruit is additionally quite attractive and is elongate and large. Fruit firmness is not very high, but its postharvest keeping ability is acceptable and it shows minimal color change (to red) of the drupelets when put in cold storage. The plant is healthy, moderately vigorous, and productive. 'Camila' is a thorny variety.

Average size information: In the study, plants were "pinched" during growth, so they were not allowed to grow freely. It is estimated that if not pinch-pruned, the primocanes would reach between about 1.7 and 2.2 m in height.

Growth: Plants have medium vegetative vigor, and erect growth habit. 'Camila' makes abundant canes, with primocanes emerging both from the crown of the plant as well as from the roots (as suckers).

Growth rate: The growth rate is moderate, with canes reaching an average of 0.8 meters in height within one month of emergence from the soil in the spring.

Productivity: High, yields average 2.0 kg and 2.9 kg of fruit per meter of row, on the floricane and on the primocane cycles, respectively.

Cold hardiness: Ultimate cold hardiness is unknown, but in Chile dormant plants have resisted midwinter lows of −3° C. without damage.

Branching height of the plants: Unknown (they are always pinched to induce branching and never left to grow to their own devices).

Canes:

*General description*.—Erect, thorny, and medium vigor.

*Cane diameter* (*indicate point of measurement*).—Floricane: Base: 1.31 cm. Midpoint: 1.04 cm. Terminal: 0.45 cm. Immature primocane: Base: 0.86 cm. Midpoint: 0.67 cm. Terminal: 0.33 cm. Mature primocane: Base: 1.25 cm. Midpoint: 0.84 cm. Terminal: 0.40 cm. Internode length: Base: 11.44 cm. Midpoint: 7.68 cm. Terminal: 5.01 cm. Thorn density/30 cm: Base: 21. Midpoint: 15. Terminal: 10.

*Primocane color*.—Base: Light green (yellow-green group 144B+GREYED-RED 180A-B (where sun strikes it)). Midpoint: Light green (yellow-green group 144C). Terminal: Light green (yellow-green group 144C.

*Floricane color*.—Base: Green with (yellow-green group 146B) brownish spots (brown group 200A-B). Midpoint: Green (yellow-green group 146B-C) with brownish spots (brown group 200A-B). Terminal: Green (yellow-green group 146B-C) with wine-colored spots (brown group 200B).

*Date of primocane emergence*.—Primocanes emerge during the first weeks of October (in Chile, at 32° 45' S. Lat., 220 m elev.) and continue emerging until the second week of November.

*Date of budbreak*.—Vegetative budbreak occurs during the second week of September (in Chile at 32° 45' S. Lat., 220 m elev.).

Foliage:

*General description*.—Leaves are green with 3 to 5 leaflets, leaves are large with double-serrate margins. The adaxial side of each leaflet is dark green with the veins being somewhat more yellowish. The abaxial side is lighter green than the adaxial side, with soft trichomes (indumentum) over the entire surface. The petioles and petiolules of each leaflet have one rank of thorns, which extend up ¼ of the length of the central vein of each leaflet.

*Leaves*.—Width: 16.85 cm. Length: 20.13 cm (including petiole). Number of leaflets: 3 to 5 per leaf.

*Leaflet*.—Width: 5.23 cm. Length: 9.46 cm (including petiolules). Margin: Doubly Serrate. Base: Cordate. Apex: Acuminate. Color: Base Adaxial: Green (yellow-green group 146-A) with the central vein of lighter green color(yellow-green group 146-B). Base Abaxial: Lighter green than the adaxial side (yellow-green group 147-B), the central vein being even lighter green with a yellowish cast (yellow-green group 144-C). Midpoint Adaxial: Green, veins of the same color and shade (yellow-green group 146-A). Midpoint Abaxial: Green (yellow-green group 147-B), but of a lighter shade than the adaxial side, yellowish colored veins (yellow-green group 144-C). Terminal Adaxial: Light green (yellow-green group 146-B), with the veins being the same color and shade. Terminal Abaxial: Light green, but a lighter shade than the adaxial side, with the veins being the same color (yellow-green group 147-C).

*Petioles*.—Length: 10.25 cm. Diameter: 2.8-3.8 mm. Color: Light Green (with a yellowish cast) (yellow-green group 144-C).

*Petiolules*.—Length: 1-4 cm. Diameter: 1.2-1.5 mm. Color: Light Green (with a slightly yellowish cast) (yellow-green group 144-C).

Flowers:

*Primocane*.—Date of bloom: (Central Chile). 10% bloom: 20th of December. 50% bloom: 30th of December. Last bloom: 2nd week of January.

*Unopened buds*.—Shape: Length: 8-10 (mm). Diameter: 2.5-3.5 (mm). Color: yellow-green group 144-B.

*Pedicels*.—Length: (mm) 35.8 mm average. Diameter: (mm) 1-2 mm. Color: yellow-green group 144-C.

*Petal color*.—Pure White (white group N155B).

*Reproductive organs*.—Stamens: The stamens are long, erect, and numerous. Pistils: Numerous. Pollen: Fertile and abundant. Ovary: Superior.

*Flower diameter*.—3-4 cm.

*Petal size*.—Width: 1.2 cm. Length: 1.8 cm.

*Average number flowers per cluster*.—6-7.

*Average number of petals per flower*.—5-9.

*Peduncle length*.—5-15 cm.

*Peduncle diameter*.—1.8-2.8 mm.

*Peduncle color*.—Green (yellow-green group 144-B).

*Floricane*.—There are no material differences noted for flower dimensions and inflorescence characteristics for floricanes compared to primocanes, but bloom times for floricanes are: Date of bloom: (Central Chile). 10% bloom: 10th of October. 50% bloom: 20th of October. Last bloom: Last week of October.

Fruit:

*General description*.—The fruit of 'Camila' stands out for its good flavor, large size, and low rate of color regression (to red drupelets) in post-harvest storage. The ratio of soluble solids to acidity averages 19 on floricane fruits and for primocane fruits, the ratio averages 23 (both values on plants grown at the experimental plot at Nogales, Chile). On both the floricane and primocane fruits there is no noticeable bitter aftertaste that is typical of eastern blackberries. The level of reversion of drupelets to a red color in postharvest storage (5° C.) is low. The fruits have an attractive appearance. They are elongated in shape and large in size. The firmness is medium, but it is acceptable.

*Primocane*.—Average first ripe date: 10th of February (for plants grown under shade cloth at 50% shade) at Nogales, Fifth Region of Valparaiso, Chile. This ripening date is seven (7) days earlier than 'APF-8' under the same conditions. The primocane harvest lasts for approximately 50 days. Size: Large (8.4 g on average). Diameter: Equator: 2.05 cm. Base pole: 2.11 cm. Terminal pole: 1.92 cm. Length: 3.01 cm. Shape: Oblong (Elongate). Drupelet size: Medium (0.42 cm average). Drupelets per fruit: average of 140. Fruit Color: black group 203-A. Seed size: Small (Length (2,5-3 mm) by width (2 mm). Firmness: medium. Flavor: Very good, sweet, without bitterness. Soluble solids: 15.1° Bx. pH: Not measured. Acidity: 0.7%. Processed quality: Not evaluated. Uses: Fresh Market. Prickles: None.

Floricane: Average first ripe date: 8th of December (for plants grown under shade cloth at 50% shade) at Nogales, Fifth Region of Valparaiso, Chile. This date is approximately 35 days before 'Navaho'. The floricane harvest lasts for about 35 days. Size: Medium (5.9 g on average). Diameter: Equator: 2.03 cm. Base pole: 21.4 cm. Terminal pole: 1.84 cm. Length: 2.85 cm. Shape: Oblong (Elongate). Drupelet size: Medium, 0.39 cm. Drupelets per fruit: not measured. Fruit Color: not measured (but should be the same as for primocanes). Seed size: Small not measured (but should be essentially the same as for primocanes). Firmness: Medium, similar to the blackberry cultivar APF-12 but firmer than 'APF-8'. Flavor: Sweet and very good flavor. Soluble solids: 11.3° Bx. pH: Not measured. Acidity: 0.6%. Processed quality: Not evaluated. Uses: Fresh Market. Prickles: None.

Thus, in some aspects, the 'Camila' blackberry is characterized by having early ripening both on floricanes and primocanes. The fruits themselves are also distinctive in that they have excellent flavor, large size, elongated shape and are visually attractive. Furthermore, the fruits have a low rate of color reversion (to red) in cold storage. The plant has good vigor and high productivity. Fruit characteristics are similar on both primocanes and floricanes, except that primocane fruits are sweeter, have higher yields, and are larger than the floricane crop.

What is claimed is:

1. A new and distinct cultivar of Blackberry plant named 'Camila' as described and illustrated herein.

* * * * *